United States Patent
Nishiura

(10) Patent No.: US 7,298,880 B2
(45) Date of Patent: Nov. 20, 2007

(54) IMAGE PROCESSING APPARATUS AND IMAGE PROCESSING METHOD

(75) Inventor: Masahide Nishiura, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 753 days.

(21) Appl. No.: 10/792,882

(22) Filed: Mar. 5, 2004

(65) Prior Publication Data

US 2004/0247165 A1    Dec. 9, 2004

(30) Foreign Application Priority Data

Mar. 7, 2003    (JP) .............................. 2003-060876

(51) Int. Cl.
*G06K 9/00*    (2006.01)
(52) U.S. Cl. ...................... 382/128; 382/130; 382/131; 128/922
(58) Field of Classification Search ................ 382/130, 382/131, 209, 219, 278; 128/128
See application file for complete search history.

(56) References Cited

U.S. PATENT DOCUMENTS

| | | | |
|---|---|---|---|
| 5,643,179 A * | 7/1997 | Fujimoto ........................ 601/2 |
| 5,669,382 A | 9/1997 | Curwen et al. |
| 6,086,532 A * | 7/2000 | Panescu et al. ............. 600/437 |
| 6,282,918 B1 * | 9/2001 | Levin et al. ................... 62/476 |
| 6,443,894 B1 * | 9/2002 | Sumanaweera et al. ..... 600/443 |
| 6,728,394 B1 * | 4/2004 | Chen et al. ................. 382/107 |

FOREIGN PATENT DOCUMENTS

| | | |
|---|---|---|
| JP | 8-106519 | 4/1996 |
| JP | 10-99334 | 4/1998 |
| JP | 10-165401 | 6/1998 |
| JP | 11-339048 | 12/1999 |
| JP | 2001-109885 | 4/2001 |
| JP | 2001-331799 | 11/2001 |

\* cited by examiner

*Primary Examiner*—Yosef Kassa
(74) *Attorney, Agent, or Firm*—Oblon, Spivak, McClelland, Maier & Neustadt, P.C.

(57) ABSTRACT

A boundary 1 of a wall in an initial image of time-series images is decided automatically or manually. A boundary 2 is generated automatically or manually in a neighbor of the other boundary of the wall. A normalized image is generated on the basis of an image pattern of a region surrounded by the boundaries 1 and 2 and registered as a template image. In each of the time-series images, boundaries 1 and 2 that generate a normalized image most similar to the template image are calculated. In this manner, wall thickness change can be calculated automatically stably and accurately even in the case where luminance change in the boundaries of a wall is obscure. This method is useful for diagnosis of heart disease etc. in medical image diagnosis.

18 Claims, 5 Drawing Sheets

IMAGE PROCESSING APPARATUS AND IMAGE PROCESSING METHOD

This application is based upon and claims the benefit of priority from the prior Japanese Patent Application No. 2003-60876 filed on Mar. 7, 2003; the entire contents of which are incorporated herein by reference.

BACKGROUND OF THE INVENTION

1. Field of the Invention

The present invention relates to an image processing apparatus and a method for aiding diagnosis using medical images.

2. Description of the Related Art

Change in thickness of cardiac muscle of a heart is a significant indicator in diagnosis of heart disease such as myocardial infarction.

As a method for measuring change in thickness of cardiac muscle, there is a method including acquiring time-series cross-sectional images of a heart and its vicinity; detecting an inner boundary and an outer boundary of the cardiac muscle by image processing; and the calculating thickness of the cardiac muscle in accordance with each image.

Artifacts, noise, etc. superposed on the images, however, make it difficult to extract the boundaries of the cardiac muscle automatically. Therefore, various methods for extracting the boundaries have been proposed.

U.S. Pat. No. 5,669,382 has disclosed a boundary extraction method using snake. Snake is a technique for obtaining a boundary by minimizing the value of an energy function defined on the basis of conditions such as change in luminance of an image and smoothness of a boundary surface.

When change in luminance is used, it is however difficult to detect a boundary low in luminance change.

Taking the case of a heart as an example, an endocardium, which is an inner boundary of cardiac muscle, is a boundary between cardiac muscle and blood. Accordingly, in the endocardium, luminance change is clear even on images obtained by various image diagnostic systems.

On the other hand, an epicardium, which is an outer boundary of cardiac muscle, is a boundary between cardiac muscle and a tissue surrounding the outside of cardiac muscle. Accordingly, in the epicardium, luminance change is often obscure on images. For this reason, it is difficult to extract both the endocardium and the epicardium accurately, stably and automatically.

JP-A-10-165401 has disclosed a technique in which a luminance distribution in a direction of wall thickness is calculated and a position exhibiting n % (e.g., 70 to 80%) of the maximum luminance is regarded as a boundary position.

Even in this technique, sufficient accuracy cannot be obtained because there is the possibility that the foot of the luminance distribution may be extended while it exceeds n % of the maximum luminance when luminance change in a boundary and its vicinity is obscure.

BRIEF SUMMARY OF THE INVENTION

Therefore, an object of the invention is to provide an apparatus and a method in which boundaries of a subject, for example, boundaries of cardiac muscle in time-series images of a heart can be obtained stably and accurately even in a case where luminance change in the boundaries of the subject is obscure.

According to a first aspect of the invention, an image processing apparatus includes an image input section, a boundary setting section, a normalized-image generating section, a template storage section, and a boundary retrieval section. The image input section is configured to input time-series images obtained by acquiring an image including a first boundary of a wall and a second boundary of the wall. The boundary setting section is configured to set the first boundary and the second boundary in an initial image of the time-series images. The normalized-image generating section is configured to generate a normalized image on the basis of an image pattern between the set first boundary and the set second boundary. The template storage section is configured to store the normalized image generated from the initial image as a template image. The boundary retrieval section is configured to search each of time-series images for the second boundary which generates the most similar normalized image to the template image.

According to a second aspect of the invention, an image processing apparatus includes an image input section, a boundary setting section, a sixth section, a normalized-image generating section, and a boundary retrieval section. The image input section is configured to input time-series images obtained by acquiring an image including a first boundary of a wall and a second boundary of the wall. The boundary setting section is configured to set the first boundary and the second boundary in an initial image of the time-series images, and set boundaries of wall parts into which the wall is divided in the initial image of time-series images. The sixth section is configured to obtain local wall thickness information of each wall part. The normalized-image generating section is configured to generate a normalized image on the basis of image patterns of the wall parts. The template storage section is configured to store the normalized image generated from the initial image as a template image. The boundary retrieval section is configured to search each of time-series images for the first boundary and the second boundary, which generate the most similar normalized image to the template image.

According to a third aspect of the invention, an image processing method detects a wall of an internal organ from time-series images. The method includes inputting time-series images obtained by acquiring an image including a first boundary of a wall and a second boundary of the wall, setting the first boundary in an initial image of the time-series images, setting the second boundary in the initial image, generating a normalized image on the basis of an image pattern between the set first boundary and the set second boundary from the initial image to store the generated normalized image as a template image, and searching each of time-series images for the first boundary and the second boundary, which generates the most similar normalized image to the template image.

DETAILED DESCRIPTION OF THE INVENTION

An image processing apparatus according to an embodiment of the invention will be described below with reference to the drawings.

This embodiment is an image processing apparatus for receiving time-series images output from an image acquiring device and performing a process of measuring wall thickness change of a subject contained in the image data. Particularly this embodiment is suitable for measurement of wall thickness change of a heart wall based on ultrasound images of the heart, the heart wall being constituted by cardiac muscle that separates the inside and outside of a heart from each other.

Figure 1:
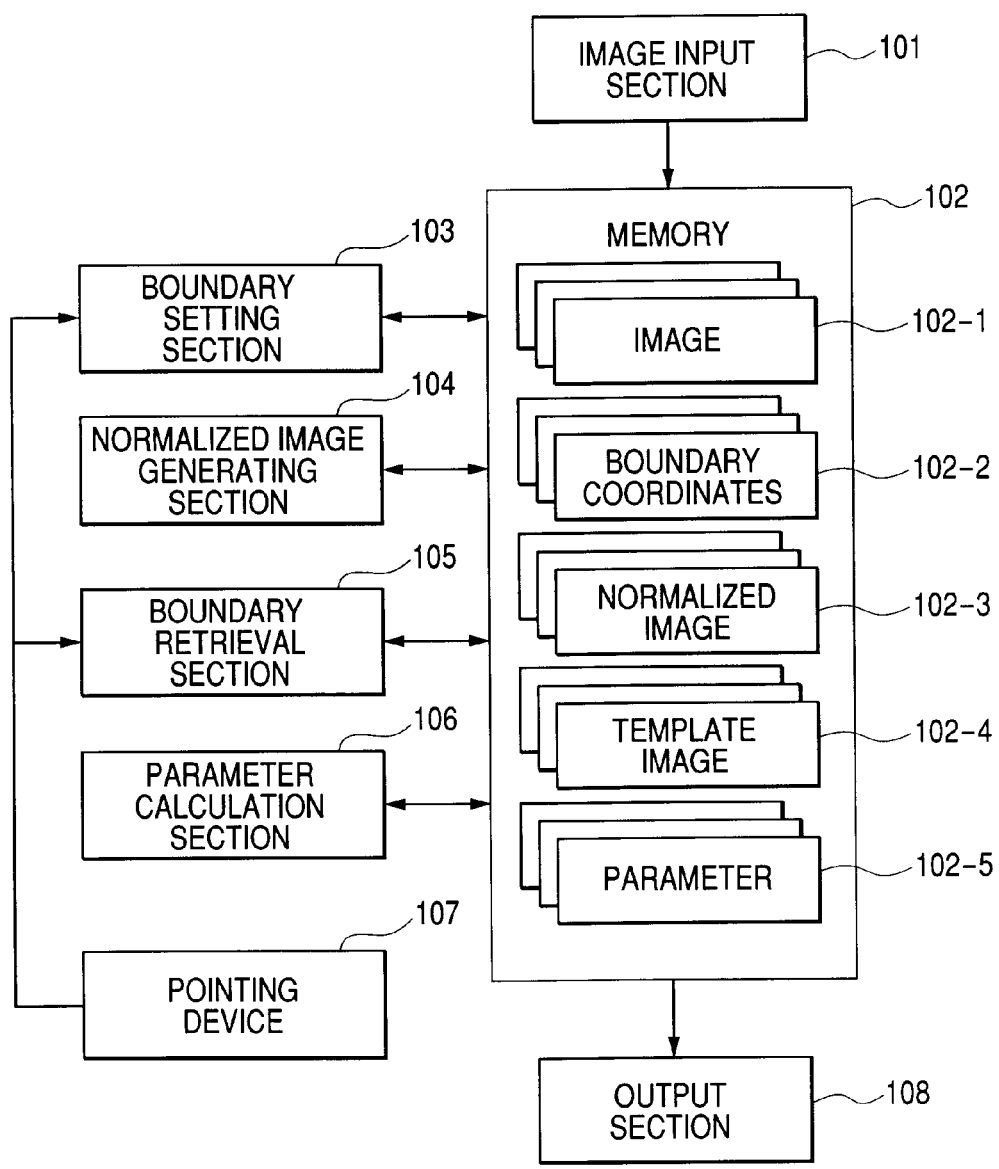
FIG. 1 is a diagram showing the configuration of an embodiment of the invention.

(Configuration) FIG. 1 is a diagram showing the configuration of this embodiment. The image processing apparatus according to this embodiment includes an image input section 101 for inputting time-series heart images obtained from an external device such as an ultrasound imaging device, and a memory 102 for storing image data and intermediate data in the middle of processing.

The image processing apparatus according to this embodiment further includes a boundary setting section 103 for detecting boundaries of the heart wall semiautomatically on the basis of luminance information of the image data, and a normalized-image generating section 104 for generating a normalized image used for retrieving the boundaries.

The image processing apparatus according to this embodiment further includes a boundary retrieval section 105 for retrieving the boundaries of the heart wall by comparing the normalized image obtained from a processed image with a template image obtained from an initial image, and a parameter calculation section 106 for calculating values useful for diagnosis, such as thickness change of the heart wall, on the basis of the decided boundaries.

The image processing apparatus according to this embodiment further includes a pointing device 107 used for various instructing operations (e.g., for setting the boundaries manually), and an output section 108 for outputting information such as obtained boundaries, thickness change of the heart wall, images in the middle of measurement of heart wall thickness, GUI, etc. to a screen.

The image input section 101 receives images acquired by the external image acquiring device (such as an ultrasound image acquiring device, an MRI image acquiring device or an X-ray image acquiring device). The images received by the image input sections 101 are frame by frame stored successively as images 102-1 in the memory 102.

The boundary setting section 103 sets the boundaries of the heart wall on the basis of the luminance information of the initial image. In this embodiment, a user uses the pointing device 107 for designating the boundaries of the heart wall.

Each of the detected boundaries is expressed as a set of representative points. The coordinates of each point detected by the boundary setting section 103 are stored as boundary coordinates 102-2 in the memory 102.

The normalized-image generating section 104 generates a normalized image by normalizing an image of a region of the heart wall surrounded by the boundaries constituted by points expressed by the boundary coordinates 102-2.

The normalization is performed by deformation into a rectangular region according to affine transformation. Respective normalized images generated by the normalized-image generating section 104 are stored as normalized images 102-3 in the memory 102. Incidentally, a normalized image of a region of the heart wall on the basis of the initial image is stored as template image 102-4 in the memory 102.

The boundary retrieval section 105 retrieves the boundaries in each frame image by using the boundaries obtained in an immediately preceding image and the template image 102-4. The details of the retrieval method will be described later (see S207 and steps following S207 which will be described later). The coordinates of points constituting the boundaries obtained by the boundary retrieval section 105 are stored as boundary coordinates 102-2 in the memory 102.

The parameter calculation section 106 calculates the wall thickness in each image by using the boundary coordinates 102-2. The parameter calculation section 106 further calculates parameters for expressing the rate of wall thickness change, the velocity of wall thickness change and deformation of the wall.

The output section 108 includes a display device such as an LCD, a CRT or a PDP. The output section 108 outputs information such as obtained boundaries, thickness change of the heart wall, images in the middle of measurement of heart wall thickness, GUI, etc. to a screen of the display device. The user uses this apparatus while watching the screen.

Figure 2:
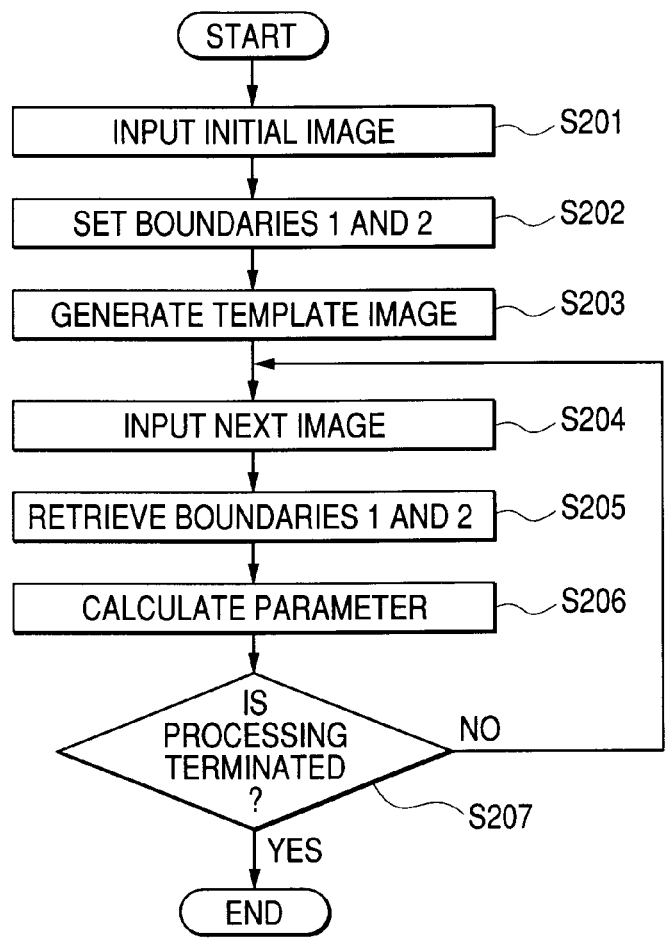
FIG. 2 is a flow chart showing a flow of processing in an embodiment of the invention.

(Operation) FIG. 2 is a flow chart showing a flow of processing according to the embodiment of the invention. The operation will be described below according to the flow of processing.

A total flow of a process of measuring wall thickness change of the heart wall will be described first. An image pattern of a heart wall portion is normalized on the basis of the boundaries of the heart wall set manually in the initial image. This normalized image is registered as a template image. After that, boundaries are retrieved from each of the time-series images so that a normalized image resembling the template image most closely can be obtained. In this manner, in each image, the boundaries of the heart wall are decided and parameters such as wall thickness change of the heart wall are calculated.

The processing will be described below in detail.

(S201) An initial image of time-series images is input in order to start measurement of wall thickness change of the heart wall.

Time-series image data from the external image acquiring device are input into this apparatus. The input image data are successively stored in the memory 102.

In this embodiment, a top frame of the input time-series image data is used as the initial image.

(S202) The boundary setting section 103 sets boundaries on both sides of the heart wall in the initial image.

In this embodiment, the inner boundary (endocardium) of the heart wall is referred to as boundary 1 and the outer boundary (epicardium) of the heart wall is referred to as boundary 2.

In this embodiment, the initial image is output to a screen, and a user designates representative points constituting each of the boundaries 1 and 2 by using the pointing device 107. Each of the boundaries 1 and 2 is set as line segments connecting these representative points.

Figure 3:
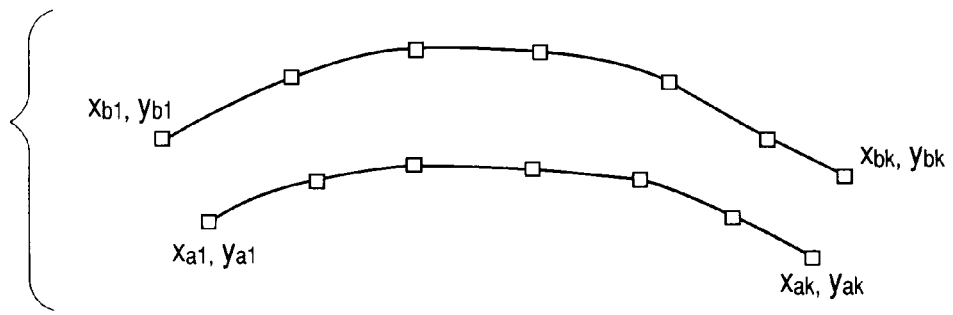
FIG. 3 shows an example of expression of contours.

FIG. 3 shows an example of the boundaries 1 and 2. In FIG. 3, characters with subscript a such as $x_{a1}$ and $y_{ak}$ show points constituting the boundary 1, and characters with subscript b such as $x_{b1}$ and $y_{bk}$ show points constituting the boundary 2.

The coordinates of points constituting each of the set boundaries 1 and 2 are stored in the memory 102.

(S203) The normalized-image generating section 104 generates a normalized image from image data located between the boundaries 1 and 2.

Figure 4:
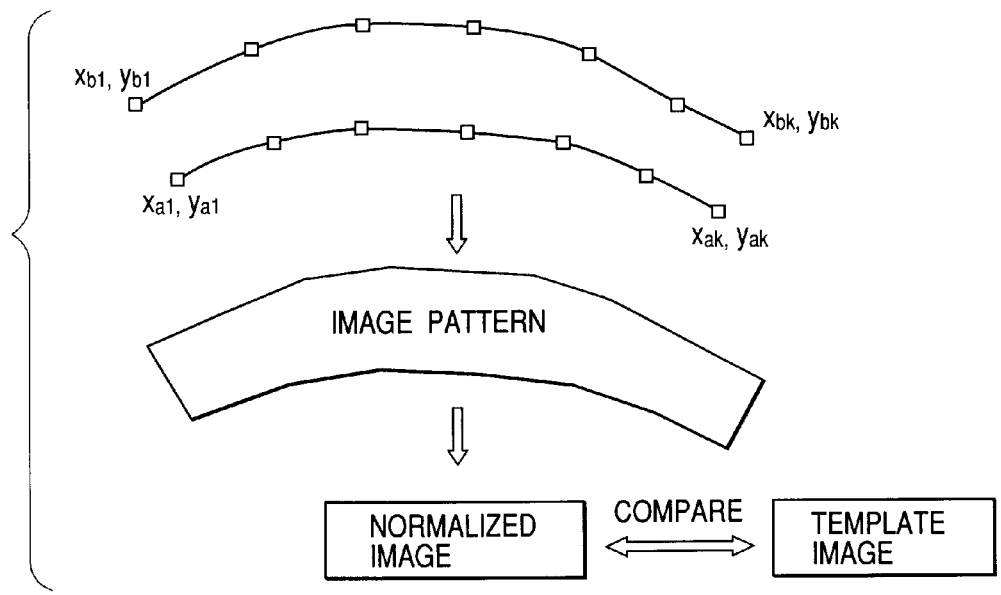
FIG. 4 is an explanatory view concerning generation of a normalized image and comparison of the normalized image with a template image.

The normalized image is generated as shown in FIG. 4. That is, even in the case where the heart wall is curved, the shape of a region is normalized to a rectangular shape having a predetermined size.

In this embodiment, normalization is performed in accordance with tetragonal regions (unit regions) into which the heart wall is partitioned by points constituting the boundaries 1 and 2. The normalized unit regions are connected to obtain a normalized image expressing the whole heart wall.

Figure 6A:
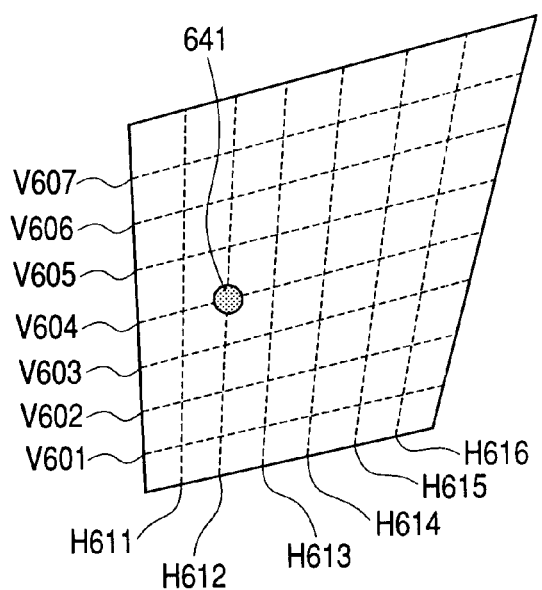
FIGS. 6A and 6B are graphs for explaining a normalizing process.
Figure 6B:
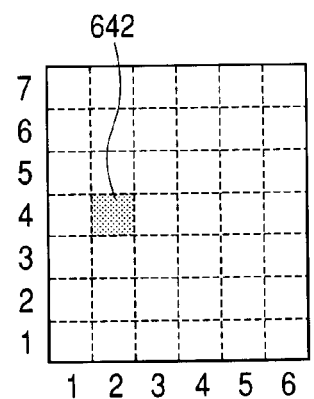

The normalizing process in this embodiment will be described with reference to FIGS. 6A and 6B. FIG. 6A is a view showing a unit region. FIG. 6B is a view showing a normalized unit region obtained by normalizing the unit region depicted in FIG. 6A.

In the following description, the case where the pixels in the normalized unit region are 7 pixels (vertically) by 6 pixels (horizontally) is taken as an example. Among sides of the unit region, sides corresponding to the boundaries 1 and 2 are taken as horizontal sides while sides corresponding to neither the boundary 1 nor the boundary 2 are taken as vertical sides.

First, equal division points for dividing each of the vertical and horizontal sides of the unit region into N equal parts are obtained. In this case, since the pixels in the normalized unit region are 7 pixels (vertically) by 6 pixels (horizontally), points for dividing the vertical sides into 8 (=7+1) equal parts and points for dividing the horizontal sides into 7 (=6+1) equal parts are obtained. As shown in FIG. 6A, attention is paid to a grid constituted by equal division lines (V601 to V607 and H611 to H616) connecting the equal division points on both sides of the vertical and horizontal sides.

Then, a pixel value of each grid point in the unit region is obtained. In this case, an average of pixel values of surrounding pixels is used as the pixel value of the grid point. Alternatively, the pixel value of a pixel containing each grid point may be used as the pixel value of the grid point or the pixel value of each grid point may be calculated on the basis of the pixel values of surrounding pixels by means of Gaussian distribution or the like.

Then, the coordinates of each grid point are expressed on the basis of the equal division lines. For example, the coordinate values of a point 641 in FIG. 6A are expressed as (2, 4) because the point 641 is a point of intersection between the fourth equal division line V604 from the bottom and the second equal division line H612 from the left.

Pixels having the coordinate values and pixel values obtained in this manner are collected to generate a normalized unit region. For example, the point 641 is transformed into a point 642 located in (2, 4) in the normalized image (see FIG. 6B).

Such processing is performed on all unit regions constituting the heart wall. The normalized unit regions obtained thus are connected to generate a normalized image. Incidentally, the connection of the normalized unit regions is performed in such a manner that vertical sides of the normalized unit regions are connected to one another while the boundary 1 of each normalized unit region is arranged so as to face upward.

The normalized image generated from the initial image is stored as a template image in the memory 102.

(S204) A next image (hereinafter referred to as image N) of the time-series images is input.

(S205) The boundary retrieval section 105 retrieves the boundaries 1 and 2 in the image N.

The retrieval of the boundaries 1 and 2 in the image N is carried out as follows. The outline of the boundary retrieval process will be described first.

Temporary boundaries 1 and 2 are set in the image N. The temporary boundaries 1 and 2 are set in the same places as the boundaries obtained in an immediately preceding image.

Then, a normalized image is generated from the temporary boundaries 1 and 2. Similarity S of the normalized image to the template image is calculated. SSD (Sum of Square Difference), which will be described later, is used as the similarity S.

The temporary boundaries 1 and 2 that give the highest one of similarities obtained by changing the temporary boundaries 1 and 2 variously are regarded as the boundaries 1 and 2 in one processed image of the time-series images.

The boundary retrieval process will be described below in detail.

Because each of the boundaries 1 and 2 is expressed as a set of points, each of the temporary boundaries 1 and 2 is expressed as a set of points in the same manner. A set X of points constituting the temporary boundaries 1 and 2 can be given by the following expression.

$$X = \{x_{a1}, y_{a1}, \ldots, x_{ak}, y_{ak}, x_{b1}, y_{b1}, \ldots, x_{bk}, y_{bk}\} \quad (1)$$

Incidentally, characters with subscript a such as $x_{a1}$, $y_{a1}$ show points constituting the temporary boundary 1, and characters with subscript b such as $x_{bk}$, $y_{bk}$ show points constituting the temporary boundary 2.

When SSD (Sum of Square Difference) of pixel values is used as a distance scale D for measuring similarity S on the assumption that f(i,j) are pixel values of the normalized image generated on the basis of the temporary boundaries 1 and 2 and $f_t(i,j)$ are pixel values of the template image, the distance D between the normalized image and the template image can be given by the following expression.

$$D = \sum_{i,j} \{f(i, j) - f_t(i, j)\}^2 \quad (2)$$

Because the distance D between the template image and the normalized image depends on the set X of points constituting the temporary boundaries, the distance D can be given by the following expression.

$$D(X) = \sum_{i,j} \{f(i, j | X) - f_t(i, j)\}^2 \quad (3)$$

The similarity S of the normalized image to the template image is maximized when the distance D is minimized. The set X of points that gives the minimum distance D is a set of points constituting the boundaries 1 and 2 in the image N.

$$X_{n+1} = X_n - \alpha \nabla D(X_n) \quad (4)$$

Because this expression cannot be solved analytically, there is used a method of obtaining a local minimum solution by numerical repetitive calculation according to a steepest descent method or the like. That is, a combination of points that minimizes the distance D is searched for while each of points constituting the boundaries is moved little by little.

If a predetermined range is entirely used for calculation based on the temporary boundaries in order to search for the combination, the volume of calculation becomes huge. Therefore, calculation is performed in such a manner that each point is moved in a direction of decreasing the distance D. When the distance D is not decreased any more though each point is moved in any direction, a decision is made that the distance D is set at a local minimum value.

Incidentally, another similarity index such as a cross correlation value or a sum of absolute difference (SAD) may be used as the similarity S.

Incidentally, the temporary boundaries need not be the same as the boundaries in an immediately preceding image. For example, the boundaries in the initial image may be directly used as the temporary boundaries or the boundaries in an image, which is near the image N in terms of time (but is not necessarily immediately precede the image N), may be used as the temporary boundaries. Alternatively, the temporary boundaries may be decided while the motions of the boundaries are estimated by some means, that is, for example, the temporary boundaries may be set at places estimated on the basis of the motions of the boundaries in the past.

(S206) The parameter calculation section 106 calculates parameters such as thickness of the heart wall, thickness change, etc. on the basis of the retrieved boundaries 1 and 2. Then, the output section 108 outputs a superposed image in forms of graph display and color coding to the display.

The thickness of the heart wall is calculated in accordance with each of line segments connecting points constituting the boundary 1. For example, with respect to a line segment A1-A2 connecting points A1 and A2, a point Bx that minimizes the distance from the points A1 and A2 is extracted from the points constituting the boundary 2 and the distance between the point Bx and a line passing through the line segment A1-A2 is calculated. The calculated distance is regarded as the thickness of the heart wall.

The parameter calculation section 106 not only calculates parameters but also generates graphs or the like by processing the parameters.

(S207) The boundary retrieval process of S205 is performed on each of the time-series images. While there is any image that has not been processed yet, the process of S204 and steps after S204 is repeated.

By the aforementioned processing, the boundaries of the heart wall in each of the time-series images are decided.

(Effect of the Embodiment) In the related art, the boundaries of the heart wall were obtained by edge detection using luminance value change in each of time-series images. The obtained boundaries were used for examining time-series change in the thickness of the heart wall.

It was however difficult to detect the outer boundary of the heart wall stably because luminance change in the outer boundary of the heart wall was obscure. That is, the positions of detected edges fluctuated because of another factor (obscurity) than the motion of the boundaries. As a result, detection of the thickness of the heart wall was apt to be unstable because of the influence of fluctuation caused by obscurity.

In this respect, according to this embodiment, attention is paid to the fact that the pattern of the heart wall little changes (in spite of variation in size) even in the case where the thickness of the heart wall changes according to the motion of the heart. That is, attention is paid to the fact that the pattern of the heart wall little fluctuates when comparison is performed after the heart wall is scaled up/down by image processing to keep the size of the heart wall constant.

Further, a normalized image generated from the initial image is stored as a template image. A normalized image generated from each image is compared with the template image (template matching) to thereby examine the heart wall.

As a result, the boundaries of the heart wall can be detected while the influence of obscurity of luminance change is minimized. That is, the boundaries of the heart wall can be detected stably. Accordingly, the thickness of the heart wall can be also calculated stably while the influence of fluctuation caused by obscurity of luminance change is minimized.

(Other Examples of the Retrieval Method Used in S205) Various methods for performing the boundary retrieval process in S205 are conceived according to the form of presentation of boundaries and the means of optimum solution. The methods will be described below by way of example.

(Example 1 of Retrieval Method) This method is particularly preferably applied to a heart image.

In the heart image, the endocardium (boundary 1) can be identified easily by means of edge detection or the like because luminance change in the image is clear in most cases. On the contrary, the epicardium (boundary 2) can hardly be identified stably by means of edge detection or the like because luminance change in the image is obscure in most cases.

Therefore, in this method, the endocardium is decided by ordinary means of edge detection using luminance change or by other means such as snake, etc.

On the other hand, the epicardium is decided by the method that has been described in the explanation of S204. In this case, only the epicardium exerts influence on the similarity of the normalized image to the template image. Accordingly, the set X of points can be given by the following expression.

$$X=\{x_{b1}, y_{b1}, \ldots, x_{bk}, y_{bk}\} \quad (5)$$

The set X of points that minimizes the distance D can be calculated in the same manner as described above in the explanation of S207. A solution can be obtained more speedily because the number of variables used is reduced by half compared with the method using both the endocardium (boundary 1) and the epicardium (boundary 2) as described above in the explanation of S204.

Incidentally, when the endocardium is decided by a method of extracting a contour on the basis of luminance change (edge) in each image, correspondence between points on the endocardium at a certain point of time t1 and points on the endocardium at an another point of time t2 is not clear. When wall thickness change is to be measured, it is however preferable to measure wall thickness change in identical wall portions.

Therefore, it is preferable to use a method of corresponding points on contour, which is divided at a position of a feature point, with each other, as described in JP-A-10-99334, which is incorporated herein by reference in its entirety.

In the case of the heart, the apex of the heart, heart valves and their vicinity can be detected as feature points easily because they are large in curvature or unique in shape.

Accordingly, points $I_C$ and $O_C$ corresponding the apex of the heart are obtained in the endocardium and epicardium obtained by the retrieval. Further, division points for equally dividing lines between ends $I_{A0}$ and $O_{A0}$ of the endocardium and epicardium and the points $I_C$ and $O_C$ corresponding the apex of the heart are obtained. Similarly, division points for equally dividing lines between the other ends $I_{B0}$ and $O_{B0}$ of the endocardium and epicardium and the points $I_C$ and $O_C$ corresponding the apex of the heart are obtained.

When, for example, each line is divided into three, points $I_{A0}$, $I_{A1}$, $I_{A2}$, $I_C$, $I_{B2}$, $I_{B1}$ and $I_{B0}$ concerning the endocardium are obtained successively viewed from one end $I_{A0}$ of the endocardium whereas points $O_{A0}$, $O_{A1}$, $O_{A2}$, $O_C$, $O_{B2}$, $O_{B1}$, and $O_{B0}$ concerning the epicardium are obtained successively viewed from one end $O_{A0}$ of the epicardium.

Among these points, points with the same subscript are regarded as points corresponding to each other. Incidentally, number of the division points may be changed suitably according to the place of measurement of wall thickness, etc.

More preferably, the endocardium may be extracted by use of a active contour model that will be described below.

Figure 7:
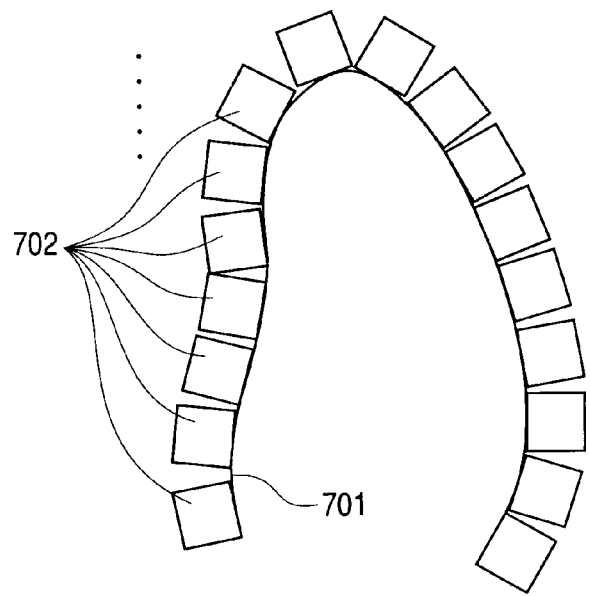
FIG. 7 is a view for explaining the outline of a active contour model capable of extracting boundaries while tracking local portions of a wall.

The active contour model capable of extracting a boundary while tracking a local portion of a wall will be described below. For example, similarity of image patterns 702 in a region near a contour 701 as shown in FIG. 7 is used in the active contour model. Accordingly, image energy in the active contour model is defined as follows:

$$E_{image} = -\int \text{Edge}(V(s)) + P_t(V(s)) ds \quad (6)$$

where V(s) means the contour 701 expressed by parameter s, Edge(V(s)) means the magnitude of luminance gradient in an image on the contour, and Pt(V(s)) means the similarity of each image pattern 702 in the region near the contour to a template pattern set in advance. Cross correlation values or the like may be used as the similarity.

When image energy is defined in this manner, the boundary contour can be extracted while the image patterns in the region near the contour are being tracked. That is, the boundary of the wall can be obtained while correspondence in local portions of the wall is taken.

(Example 2 of Retrieval Method) In order to obtain a higher speed, in the boundary setting section 103, a subject of measurement in wall thickness change of the heart wall is divided into a plurality of segments on the basis of the endocardium and epicardium set in the initial image. The epicardium may be expressed on the basis of the thickness t and a displacement parameter s from the endocardium for the boundaries of each segment. A direction of the displacement parameter s is different from that of the thickness t, and preferably is perpendicular to that of the thickness t.

Incidentally, in each image, the endocardium is decided by ordinary means of edge detection using luminance change or by other means such as snake.

When the endocardium is decided by a method of extracting the contour on the basis of luminance change (edge) in each image, correspondence between points on the endocardium at a certain point of time t1 and points on the endocardium at another point of time t2 is not clear. In this method, it is however necessary to set the correspondence because the epicardium is expressed on the basis of the thickness t and a displacement parameter s from the endocardium.

Therefore, the correspondence is set in the same manner as described above in Example 1 of Retrieval Method. That is, there is used a method of corresponding points on contour parts, which is divided at the position of the feature point with each other.

First, division points for dividing the endocardium and epicardium on the basis of a feature point are obtained in the endocardium and epicardium set in the initial image and are associated with each other. Then, the heart wall is divided into segments by the positions of points corresponding to each other, and the thickness t and the displacement parameter s are obtained in accordance with each of the corresponding points.

After that, in each image, division points for dividing the endocardium decided by means of edge detection or the like on the basis of the position of the feature point are obtained in the same manner as in the initial image. Because a division point of the epicardium is located in a position far by the optimum thickness t and the optimum displacement parameter s from each division point of the endocardium, the optimum values are calculated while the thickness t and the displacement parameter s are changed.

The optimum values of s and t are values at which a normalized image of highest similarity to the template image obtained on the basis of segments of the initial image can be obtained from the image N.

Figure 5:
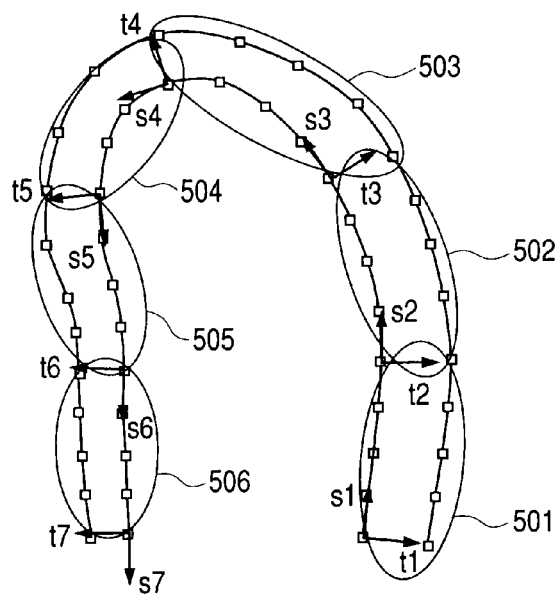
FIG. 5 shows an example of expression of boundaries by small number of parameters.

FIG. 5 is a view for explaining a state in which a cardiac muscle image is divided into six segments 501 to 506. In FIG. 5, points on the epicardium are expressed for the boundaries of each segment on the basis of the thickness t and the displacement parameter s from points on the endocardium.

When the epicardium is expressed in this manner, a set of the coordinates of points constituting the epicardium can be given by the following expression.

$$X = \{t_1, s_1, \ldots, t_k, s_k\} \quad (7)$$

In the example shown in FIG. 5, only fourteen parameters are required because of k=7. Because the boundaries can be expressed by far smaller number of parameters than the number of parameters in the expression 5 or 1, a solution can be obtained more speedily.

Incidentally, the endocardium may be extracted by use of the active contour model as explained in Example 1 of Retrieval Method.

(Example 3 of Retrieval Method) Although Example 2 of Retrieval Method has shown the case where a subject of measurement of wall thickness change of the heart wall is divided into segments so that points expressing the boundary 2 are set for the boundaries of each segment, the boundaries may be expressed by smaller number of parameters according to an interpolating method using a splined curve or the like.

Although the description has been made while the heart is taken as an example, thickness change of a wall or the like can be also detected in other internal organs (such as the stomach, the liver, the urinary bladder, the kidney and the uterus) and an unborn baby as well as the heart.

(Modification) This embodiment may be provided as a mode for a medical work station containing not only a process of measuring wall thickness change of the heart wall but also other image measuring process and a data management function such as filing.

Alternatively, a series of heart wall thickness change measuring steps for image data (e.g., functions of the boundary setting section 103, the normalized-image generating section 104, the boundary retrieval section 105 and the parameter calculation section 106) may be implemented by a program executed by a general-purpose computer. Or the series of heart wall thickness change measuring steps for image data may be implemented in the form in which the functions are incorporated into an image diagnostic system.

Although the description has been made on the case where the user sets the boundaries manually in the boundary setting section 103 of this apparatus, the boundaries may be detected automatically by applying a method called snake or an ordinary edge detection method to the initial image. In this case, configuration may be made so that the user can correct the boundaries by using the pointing device 107 if the boundaries automatically detected cannot be always reliable due to the obscure boundaries.

Figure 8:
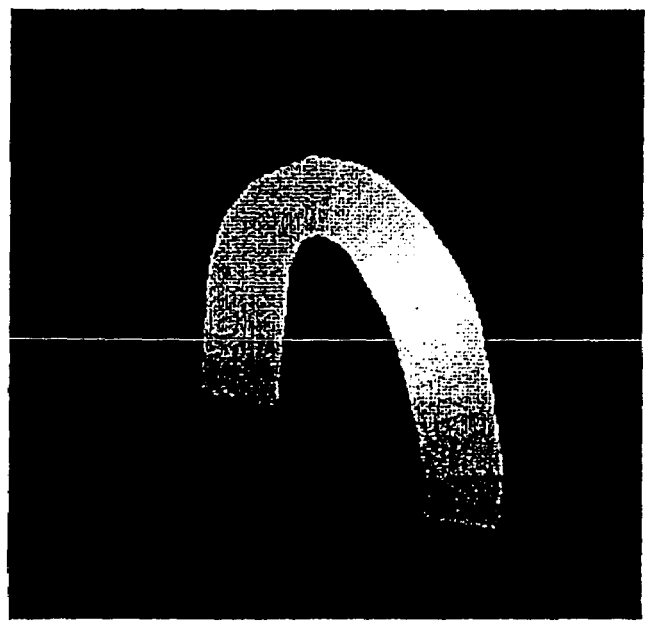
FIG. 8 shows an example of display of a heart image in a gray scale manner according to the thickness of the heart wall.

In the output section 108 of this apparatus, gray scale or colors may be assigned according to the thickness of the heart wall to each image to display a heart wall image. FIG. 8 shows an example of expression of a monotone image in a gray scale manner according to the thickness of the heart wall. For example, a thick portion is displayed with being shaded, a thin portion is displayed with being lightened, and an intermediate portion is displayed with intermediate tone. In this manner, by only one glance at intensive change in gray scale, a judgment can be made as to whether cardiac muscle operates actively (repeats expansion and contraction) or not. This is useful for diagnosis.

Gray scale may be assigned to an image according to thickness change of the heart wall per predetermined unit time instead of the thickness of the heart wall itself. In this case, the thickness of each portion of the heart wall per predetermined unit time is stored in the memory 102 in advance. The degree of thickness change is calculated on the basis of the data stored in the memory 102.

As described above, in accordance with the embodiments of the invention, deformation of a wall is obtained on the basis of not only the edge of the image but also an image pattern. As a result, even in the case where the wall had such obscure boundaries that the detected edge fluctuated in the related art, the boundaries can be detected stably.

What is claimed is:

1. An image processing apparatus comprising:
   an image input section configured to input time-series images obtained by acquiring an image of an internal organ including a first boundary of a wall and a second boundary of the wall;
   a boundary setting section configured to set the first boundary and the second boundary in an initial image of the time-series images;
   a normalized-image generating section configured to generate a normalized image on the basis of an image pattern between the set first boundary and the set second boundary;
   a template storage section configured to store the normalized image generated from the initial image as a template image; and
   a boundary retrieval section configured to search each of time-series images for the second boundary which generates the most similar normalized image to the template image.

2. The image processing apparatus according to claim 1, wherein the boundary retrieval section searches each of time-series images for the first boundary and the second boundary, which generate the most similar normalized image to the template image, in each of time-series images.

3. The image processing apparatus according to claim 2, wherein the boundary retrieval section includes:
   a first section configured to set a first temporary boundary and a second temporary boundary in each of time-series images on the basis of the first boundary and the second boundary in an image input preceding each of time-series image; and
   a second section configured to search each of time-series images for a region in which the most similar normalized image to the template image is generated, while changing coordinates of points representing the first temporary boundary and the second temporary boundary.

4. The image processing apparatus according to claim 2, wherein the boundary retrieval section includes:
   a third section configured to detect the first boundary in each of time-series images on the basis of luminance values thereof;
   a fourth section configured to set a second temporary boundary in each of time-series images on the basis of the second boundary in an image input preceding each of time-series images; and
   a fifth section configured to search each of time-series images for a region in which the most similar normalized image to the template image is generated, while changing coordinates of points representing the second temporary boundary.

5. The image processing apparatus according to claim 2, wherein the boundary retrieval section includes:
   a third section configured to detect the first boundary in each of time-series images on the basis of luminance values thereof;
   a fourth section configured to set a second temporary boundary in each of time-series images on the basis of the second boundary in the initial image; and
   a fifth section configured to search each of time-series images for a region in which the most similar normalized image to the template image is generated, while changing coordinates of points representing the second temporary boundary.

6. The image processing apparatus according to claim 2, wherein the boundary retrieval section includes:
   a third section configured to detect the first boundary in each of time-series images on the basis of luminance values thereof;
   a fourth section configured to estimate a second temporary boundary in each of time-series images on the basis of the second boundaries in the preceding images of each time series image; and
   a fifth section configured to search each of time-series images for a region in which the most similar normalized image to the template image is generated, while changing coordinates of points representing the second temporary boundary.

7. An image processing apparatus comprising:
   an image input section configured to input time-series images obtained by acquiring an image of an internal organ including a first boundary of a wall and a second boundary of the wall;
   a boundary setting section configured to set the first boundary and the second boundary in an initial image of the time-series images, and set boundaries of wall parts into which the wall is divided in the initial image of time-series images;
   a sixth section configured to obtain local wall thickness information of each wall part;
   a normalized-image generating section configured to generate a normalized image on the basis of image patterns of the wall parts;
   a template storage section configured to store the normalized image generated from the initial image as a template image; and
   a boundary retrieval section configured to search each of time-series images for the first boundary and the second boundary, which generate the most similar normalized image to the template image.

8. The image processing apparatus according to claim 2, wherein:
the image of the wall is an image of section of a cardiac muscle;
the first boundary is an epicardial boundary; and
the second boundary is an endocardial boundary.

9. The image processing apparatus according to claim 8, wherein the boundary retrieval section includes:
a first section configured to set an epicardial temporary boundary and an endocardial temporary boundary in each of time-series images on the basis of the epicardial boundary and the endocardial boundary in an image input immediately preceding each of time-series image; and
a second section configured to search each of time-series images for a region in which the most similar normalized image to the template image is generated, while changing coordinates of points representing the epicardial temporary boundary and the endocardial temporary boundary.

10. The image processing apparatus according to claim 8, wherein the boundary retrieval section includes:
a third section configured to detect the endocardial boundary in each of time-series images on the basis of luminance values thereof;
a fourth section configured to set an epicardial temporary boundary in each of time-series images on the basis of the epicardial boundary in an image input preceding each of time-series images; and
a fifth section configured to search each of time-series images for a region in which the most similar normalized image to the template image is generated, while changing coordinates of points representing the epicardial temporary boundary.

11. The image processing apparatus according to claim 8, wherein the boundary retrieval section includes:
a third section configured to detect the endocardial boundary in each of time-series images on the basis of luminance values thereof;
a fourth section configured to set an epicardial temporary boundary in each of time-series images on the basis of the epicardial boundary in the initial image; and
a fifth section configured to search each of time-series images for a region in which the most similar normalized image to the template image is generated, while changing coordinates of points representing the epicardial temporary boundary.

12. The image processing apparatus according to claim 8, wherein the boundary retrieval section includes:
a third section configured to detect the endocardial boundary in each of time-series images on the basis of luminance values thereof;
a fourth section configured to estimate an epicardial temporary boundary in each of time-series images on the basis of the epicardial boundaries in the preceding images of each time series image; and
a fifth section configured to search each of time-series images for a region in which the most similar normalized image to the template image is generated, while changing coordinates of points representing the epicardial temporary boundary.

13. The image processing apparatus according to claim 7, wherein the boundary setting section sets boundaries of wall parts into which the cardiac muscle is divided in an initial image of time-series images,
the image processing apparatus further comprising:
a sixth section for obtaining local wall thickness information of each wall part, wherein the boundary retrieval section searches each of time-series images for the region in which the most similar normalized image to the template image is generated, while changing the local wall thickness information of each wall part.

14. An image processing method for detecting a wall of an internal organ from time-series images, the method comprising:
inputting time-series images obtained by acquiring an image including a first boundary of a wall and a second boundary of the wall;
setting the first boundary in an initial image of the time-series images;
setting the second boundary in the initial image;
generating a normalized image on the basis of an image pattern between the set first boundary and the set second boundary from the initial image to store the generated normalized image as a template image; and
searching each of time-series images for the first boundary and the second boundary, which generate the most similar normalized image to the template image.

15. The image processing method according to claim 14, wherein the searching includes:
setting a first temporary boundary and a second temporary boundary in each of time-series images on the basis of the first boundary and the second boundary in an image input preceding each of time-series images; and
searching each of time-series images while changing coordinates of points representing the first temporary boundary and the second temporary boundary.

16. The image processing method according to claim 14, wherein the searching includes:
detecting the first boundary in each of time-series images on the basis of luminance values;
setting a first temporary boundary in each of time-series images on the basis of the first boundary and the second boundary in an image input preceding each of time-series images; and
searching each of time-series images while changing coordinates of points representing the second temporary boundary.

17. The image processing method according to claim 14, further comprising:
obtaining local wall thickness information of wall parts into which the wall is divided, before the searching, wherein:
the searching includes searching each of time-series images for a region in which the most similar normalized image to the template image is generated, while changing the local wall thickness information of each wall part.

18. The image processing apparatus according to claim 8, further comprising:
a parameter calculation section configured to calculate the thickness of each parts of the cardiac muscle on the basis of the determined endocardial boundary and the determined epicardial boundary in each time-series image; and
an output section configured to output images obtained by adding one of gray scale and colors to the cardiac muscle of the time-series images in accordance with the thickness of the each part of the cardiac muscle.

* * * * *